United States Patent [19]

Devauchelle et al.

[11] Patent Number: 5,565,333
[45] Date of Patent: Oct. 15, 1996

[54] PLASMID REPLICATION ORIGIN INCREASING THE COPY NUMBER OF THE PLASMID CONTAINING THE SAID ORIGIN

[75] Inventors: Gérard Devauchelle, Saint-Christol-lès-Alès; Laurence Garnier, Norières-les-Avignon; Martine Cerutti, Saint-Christol-lès-Alès; Viviane Valverde; Jean-Michel Masson, both of Toulouse, all of France

[73] Assignees: Institut National de la Recherche Agronomique (INRA); Centre National de la Recherche Scientifique (CNRS), both of Paris Cedex, France

[21] Appl. No.: 175,354
[22] PCT Filed: Jul. 10, 1992
[86] PCT No.: PCT/FR92/00671
§ 371 Date: May 16, 1994
§ 102(e) Date: May 16, 1994
[87] PCT Pub. No.: WO93/01293
PCT Pub. Date: Jan. 21, 1993

[30] Foreign Application Priority Data

Jul. 12, 1991 [FR] France ................................. 91 08836

[51] Int. Cl.⁶ ............................ C12P 21/06; C12P 19/36; C07H 21/04; C12N 15/00
[52] U.S. Cl. .................. 435/69.1; 435/91.2; 435/91.21; 435/172.1; 435/320.1; 536/23.1; 536/24.1
[58] Field of Search .................... 435/320.1, 172.1, 435/91.2, 91.21, 69.1; 536/23.1, 24.1

[56] References Cited

PUBLICATIONS

Drocourt et al. Casettes of the *Streptoalloteichus hindustanusble* Gene for Transformation of Lower and Higher Eukaryotes to Phleomycin Resistance 18 (13): 4009. 1990. Nucleic Acids Research.
Sequence Search on MPSRCH, Locus: SYNSHBL.
Sambrook et al. Molecular Cloning: A Laboratory Manual. 1989. pp. 1–21–1–24; 1–74–1–75; 12–4–12–10.

*Primary Examiner*—George Elliott
*Assistant Examiner*—Thanda Wai
*Attorney, Agent, or Firm*—Oblon, Spivak, McClelland, Maier & Neustadt, P.C.

[57] ABSTRACT

A DNA sequence derived by the mutation from a ColE1-type replication origin is provided, wherein the sequence is characterized in that it includes at least one of the following mutations, which are defined in relation to the wild ColE1 origin: a Guanine to Adenine transversion in position 2976; and a Guanine deletion in position 3057. This sequence increases the number of copies of the plasmids which include it. Plasmids containing the replication origin, and their uses in the amplification of DNA sequences and the production of polypeptides by genetic engineering, are also disclosed.

15 Claims, 6 Drawing Sheets

```
TAGAAGGACA GTATTTGGTA TCTGCGCTCT GCTGAAGCCA
2970       2980       2990       3000
   GTTACCTTCG GAAAAGAGT TGGTAGCTCT TGATCCGGCA
3010       3020       3030       3040
   AACAAACCAC CGCTGGTAGC GGTGGTTTTT TTGTTTGCAA
3050       3060       3070       3080      3089
```

*FIG. 1a*

```
TAGAAGaACA GTATTTGGTA TCTGCGCTCT GCTGAAGCCA
2970       2980       2990       3000
   GTTACCTTCG GAAAAGAGT TGGTAGCTCT TGATCCGGCA
3010       3020       3030       3040
   AACAAACCAC CGCTGGTAGC GGTGGTTTTT TTGTTTGCAA
3050       3060       3070       3080      3089
```

PLASMID REPLICATION ORIGIN INCREASING THE COPY NUMBER OF THE PLASMID CONTAINING THE SAID ORIGIN

BACKGROUND OF THE INVENTION

1. Field of the Invention

The invention relates to a plasmid replication origin, and to plasmids containing the said origin.

2. Discussion of the Background

Plasmids are extrachromosomal circular DNA fragments which are transferable from one bacterium to another, and whose replication occurs independently of that of the bacterial chromosome. A given plasmid can be present in a high copy number inside a bacterial cell. The copy number is a genetic characteristic of each plasmid. For example, in the ColE1-type plasmids (such as plasmids of the families pBR, pUC, and the like), the copy number is under the control of a DNA region corresponding to the replication origin of the plasmid (ORI) which extends approximately between bases 2940 and 3130 (numbering of the bases of pBR322 proposed by PEDEN [Gene, 22 (1983) 277–280]). A portion of this region, situated between bases 2970 and 3089 is transcribed into RNAs called RNAI and RNAII. RNAI, in particular, is thought to play a role in the regulation of the plasmid copy number.

Plasmids are commonly used in genetic engineering as vectors for the cloning and expression of foreign genes in bacteria.

It is particularly desirable, for this purpose, to have available plasmids present in high copy number, either in order to obtain the foreign DNA in a large quantity (for example in order to allow its sequencing), or in order to increase the quantity of the product of expression of the said foreign gene.

A conventional technique for obtaining a large quantity of plasmids is to add to the bacteria cultures chloramphenicol which prevents cell multiplication by blocking translation, without affecting plasmid replication. Nevertheless, since chloramphenicol also interferes with the translation of the foreign gene, this method is not optimal when an increase in the expression of the said gene is desired.

Plasmids carrying a mutation which influences the copy number have been described in the literature. BOROS et al. [Gene, 30, 257–260 (1984)] thus describe a mutant plasmid derived from pBR322. The copy number of this plasmid per cell is increased by about 200-fold relative to the copy number of pBR322. This increase in the number of copies results from a G to T transversion localized in position 3075 on the 2846–3363 HinfI fragment, close to the 3' end of the sequence transcribed into RNAI. MUESINO et al. [Cell, 24, 235–242, (1981)] had earlier demonstrated the same mutation in the plasmid ColE1 (whose replication origin is similar through the sequence to that of pBR322), also with, as effect, an increase in the copy number of the said plasmid (up to 300 per cell).

However, such an amplification of the copy number has certain disadvantages which limit its practical applications. This indeed results in:

an increased risk of toxicity for the host bacterium, by too high an expression of the recombinant genes carried by the plasmid, which is in addition generally accompanied by the production of precipitation granules and makes it impossible, in addition, to envisage the expression of periplasmic proteins;

an increased probability of uncontrolled recombinations between plasmids, in particular for the plasmids carrying certain specific sequences (for example of phage origin).

Now, during experiments for mutagenesis of the plasmid pUC9, the inventors have obtained plasmids carrying mutations in the ORI sequence of the replication origin, and have observed that, surprisingly, the copy number of these plasmids is 10 to 25-fold higher than that of the original plasmid.

The inventors have sequenced the replication origins of the mutated plasmids, and have localized the corresponding mutations.

SUMMARY OF THE INVENTION

The subject of the present invention is a DNA sequence, derived by mutation from a ColE1-type replication origin, which sequence is characterized in that it comprises at least one of the following mutations, defined with respect to the wild type ColE1 origin:

a Guanine → Adenine transversion in position 2976 a deletion of a Guanine in position 3057.

The position of the mutations is indicated according to the numbering of the bases of pBR322 proposed by PEDEN [Gene 22 (1983) 277–280].

According to a preferred embodiment of a DNA sequence conforming to the invention, the said sequence carries two mutations defined above.

BRIEF DESCRIPTION OF THE DRAWINGS

FIG. 1 shows in (1a) the sequence of the 2970–3089 region of a wild type replication origin of pBR322 (SEQ ID NO:1), and in (1b) a sequence conforming to the invention, carrying the two mutations defined above (SEQ ID NO:2).

DESCRIPTION OF THE PREFERRED EMBODIMENTS

The inventors have, in addition, observed that a mutated sequence conforming to the invention could be inserted into other plasmids in place of the corresponding sequence of the initial replication origin, and that an increase in the copy number of the recombinant plasmids thus obtained results therefrom.

The present invention therefore encompasses plasmids characterized in that their replication origin, of the ColE1 type, comprises a mutated sequence as defined above.

Figure 1A:
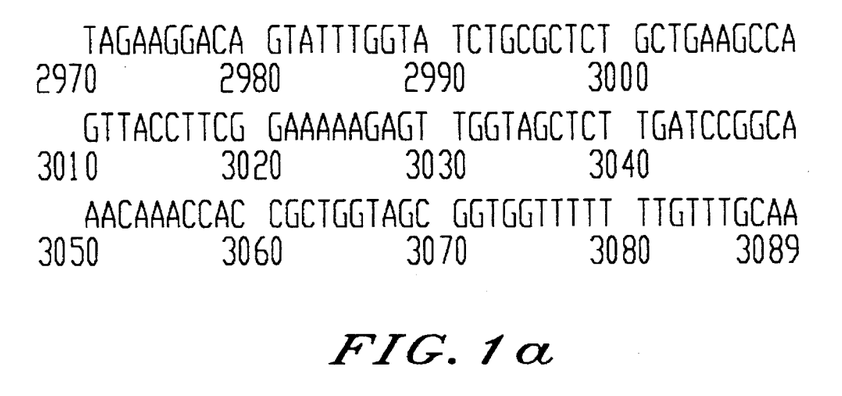
Figure 1B:
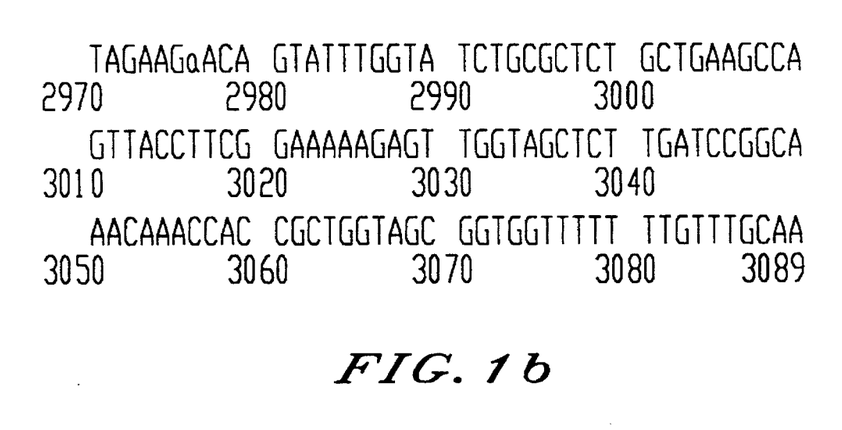
Figure 2:
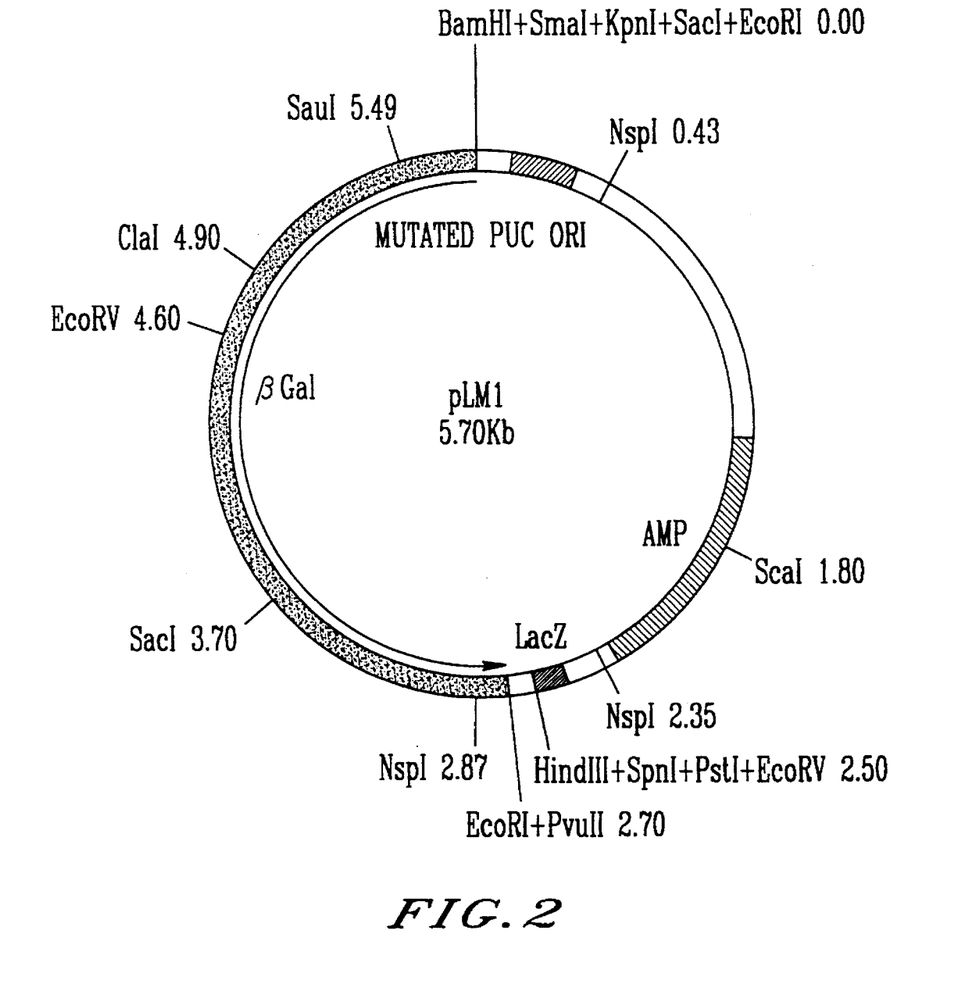
FIGS. 2, 3, and 4 represent plasmids conforming to the invention called pLM1, pLM2 and pLM3, respectively.
Figure 3:
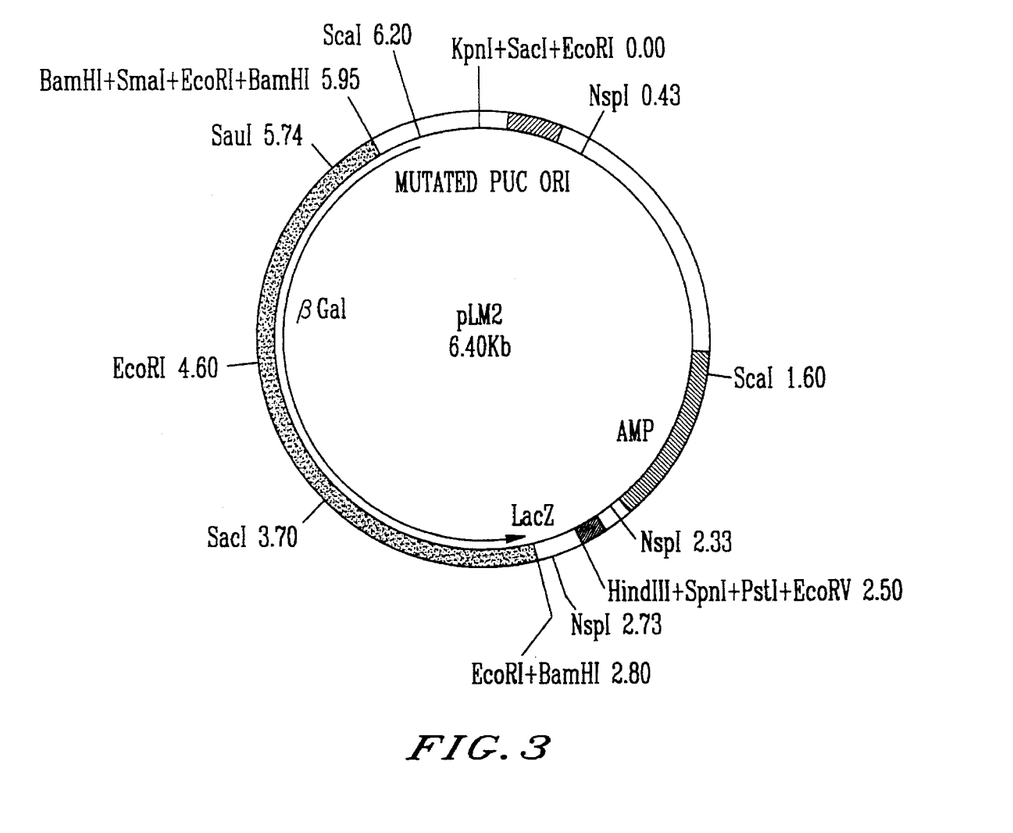
Figure 4:
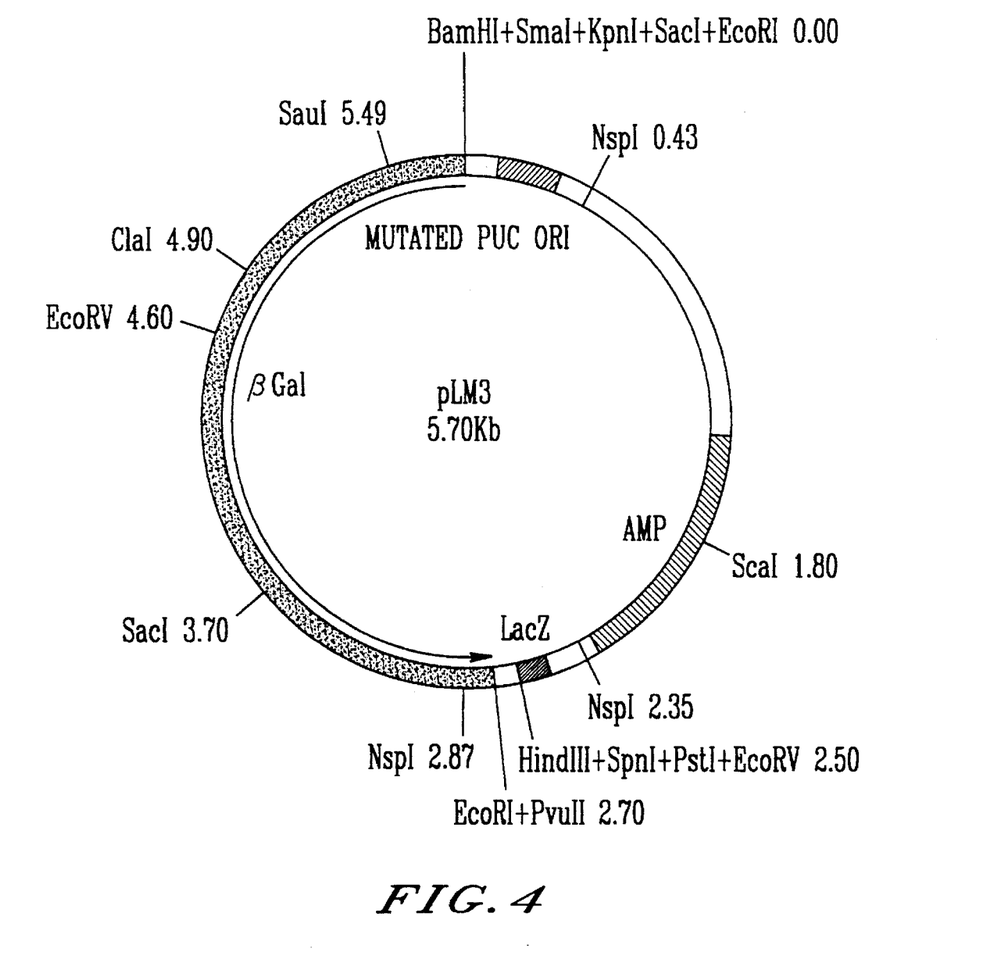

FIGS. 2, 3 and 4 represent plasmids conforming to the invention called pLM1, pLM2 and pLM3 respectively. Plasmids pLM1, pLM2 and pLM3 are derived from the plasmid pUC9 by mutation, as defined above, of the replication origin, and also comprise the complete β-galactosidase gene, flanked by a polylinker, and placed under the control of the promoter of the LacZ gene.

Other plasmids conforming to the invention can be easily obtained, for example from plasmids carrying a ColE1 type replication origin, by a site-directed mutagenesis technique, or alternatively from a plasmid such as pML1 by excising from the latter the segment of mutated DNA and by inserting it in place of the segment of wild type DNA corresponding to the recipient plasmid. It will appear to a person skilled in the art that it is also possible to obtain a DNA segment conforming to the invention by oligonucleotide synthesis, according to techniques known per se and to insert it in the recipient plasmid.

The techniques which permit this insertion are also known per se. It is possible to mention for example the techniques using homologous recombination, or alternatively excision from a restriction fragment carrying the non-mutated origin and its replacement by a fragment carrying the mutated origin.

Figure 5A:
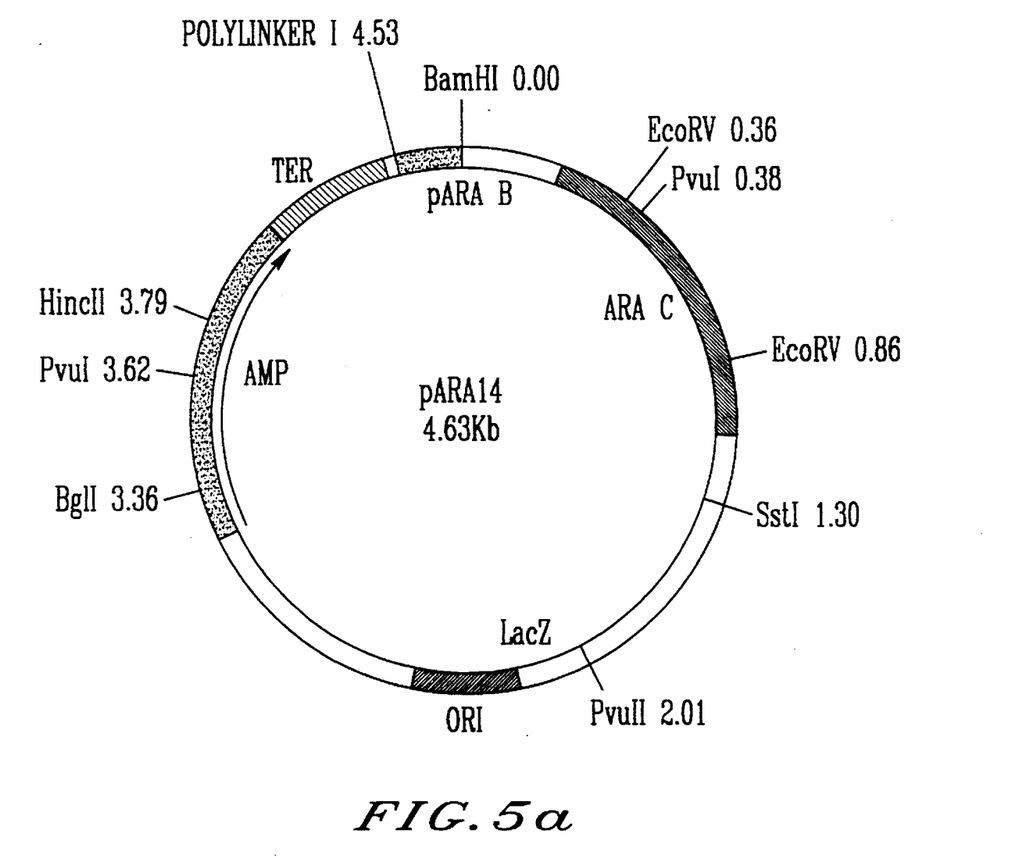
FIGS. 5a and 5b represent the plasmids called pARA14 and pARA15, respectively.
Figure 5B:
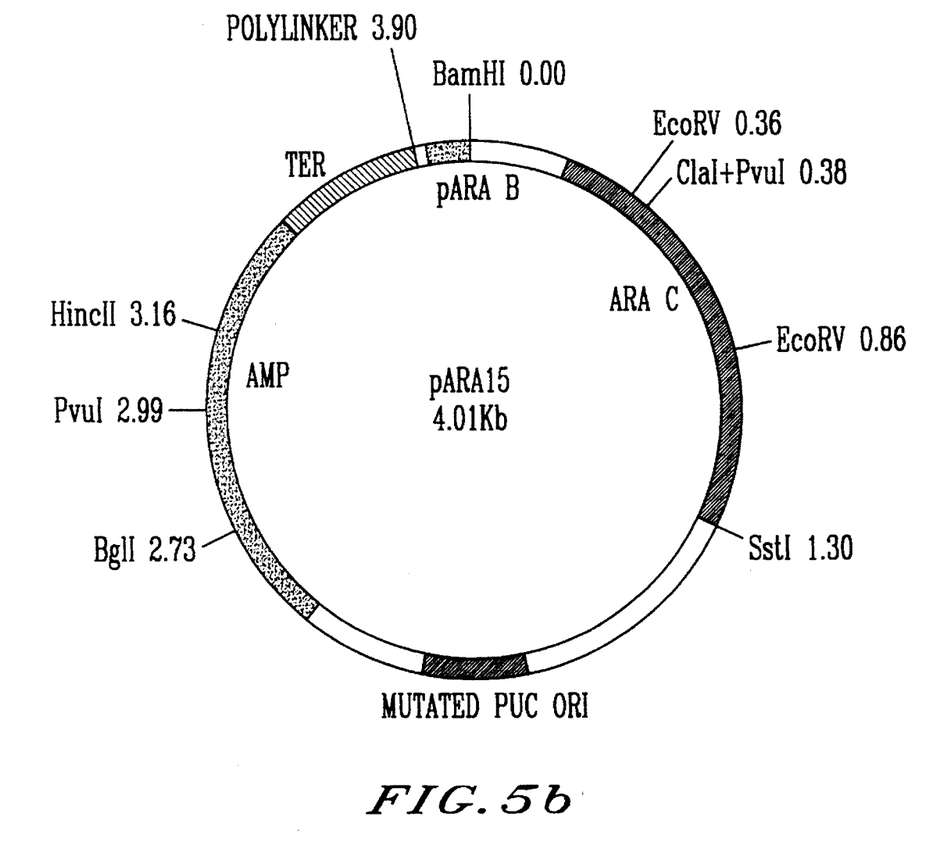

FIG. 5b represents the plasmid pARA 15 obtained in such a manner from a plasmid called pARA 14 (FIG. 5a) which is an expression vector containing the replication origin of pBR322, an ampicillin-resistance gene and an arabinose-inducible promoter.

The recipient plasmids which can be used for the construction of plasmids conforming to the invention are generally all plasmids compatible with a ColE1-type replication origin.

The copy number of the plasmids thus obtained is at least multiplied by 10 relative to the corresponding "wild type" plasmids. The expression of the foreign genes placed in these plasmids increases in the same proportions. The promoters which control the expression of these genes remain inducible.

In addition, this relatively small increase in the copy number is optimal for obtaining a satisfactory expression of an exogeneous gene inserted in the plasmid, since it makes it possible to avoid the disadvantages (mentioned above with respect to the plasmids obtained by BOROS et al.) resulting from a too high copy number.

The host strains suitable for the multiplication of the plasmids conforming to the invention and to the expression of the genes carried by these plasmids are the same as those which permit the multiplication of the corresponding wild type plasmids and the expression of the genes which they carry, and the behaviour and the growth of the strains transformed by the plasmids conforming to the invention are identical to those of the strains carrying the wild type plasmids.

In addition, there is no reversion of the mutation, and the phenotype characterized by the increase in the copy number remains stable over generations.

The subject of the present invention is in addition a process for the multiplication of the plasmids conforming to the invention, which process is characterized in that, in a first step, an appropriate host bacterial strain is transformed with at least one of the said plasmids, and in a second step, the said bacterial strain is cultured.

The invention also encompasses:

A process for the amplification of a DNA sequence, which process is characterized in that, in a first step, the said sequence is inserted in a plasmid conforming to the invention, and in that, in a second step, the multiplication of the said plasmid is carried out as indicated above.

A process for the production of polypeptides by genetic engineering, which process is characterized in that, in a first step, the gene encoding the said polypeptide is inserted in a plasmid conforming to the invention, in a second step, an appropriate host bacterial strain is transformed with the said plasmid, and in a third step, the said bacterial strain is cultured under conditions appropriate for the expression of the said gene.

EXAMPLES

The present invention will be understood more clearly with the aid of the additional description below, which refers to examples of producing plasmids carrying the replication origin conforming to the invention.

It goes without saying, however, that these examples are given solely by way of illustration of the subject of the invention, and do not constitute in any manner a limitation thereof.

Example 1

Preparation of Plasmids Conforming to the Invention

The plasmid pARA 15 is derived from the plasmid pARA 14 by replacing the initial replication origin of the latter (which is that of pBR322) by the mutated replication origin conforming to the invention. To do this, a 2060-bp SstI/BglI fragment of pARA 14, comprising its replication origin, is excised and replaced by a 1430 bp SstI/BglI fragment derived from pLM3, comprising the replication origin conforming to the invention.

FIG. 5 represents the plasmid pARA 14 (5a), carrying a wild type replication origin and the plasmid pARA 15 (5b) carrying a replication origin conforming to the invention.

In the plasmids pARA 14 and pARA 15, the foreign genes which it is desired to express are under the control of an arabinose-inducible promoter.

Example 2

Evaluation of the Copy Number of the Plasmids Conforming to the Invention a) Measurement of the quantity of plasmid DNA The DNA was extracted from cultures of *E. coli* TG1 cells (2 ml), harvested at 2.3 $OD_{600}$ U. The cells were lysed with a mixture of lysozyme, detergent and sodium hydroxide. After centrifugation, the plasmid DNA contained in the supernatant was separated from the proteins by a phenol extraction followed by a chloroform treatment. The pure plasmid DNA is then precipitated with ethanol, the precipitate is centrifuged and dried under vacuum, and then redissolved in 50 μl of buffer (10 mM tris, 1 mM EDTA, pH8) for each sample. Extracts of *E. coli* TG1 cells containing either the plasmid pARA 14 (control strain), or the plasmid pARA 15 were prepared in this manner.

5 μl of each preparation were incubated for 2 hours at 37° C. with 5 units of restriction enzyme XhoI. The hydrolysis product was then loaded onto a 1% agarose gel and subjected to electrophoresis in TBE buffer (containing 20 μg of ethidium bromide per liter) for 2 hours at 250 volts. The gel is then subjected to irradiation with ultraviolet rays. The intensity of fluorescence emitted by the DNA bands in the gel is proportional to the quantity of DNA, for a given size of fragment, and therefore reflects the relative copy number of plasmids.

Examination of the gels shows that there are at least 10 times more plasmid DNA with the strains carrying the mutated plasmid than with the control strains.

Example 3

Measurement of the Expression of the Exogeneous Genes Inserted in the Plasmids Conforming to the Invention a) Expression of the β-lactamase gene In another experiment, the β-lactamase (expressed from the bla gene present in each of the plasmids pARA 14 and pARA 15 and conferring an ampicillin resistance) produced in the exponential growth phase was assayed for an *E. coli* TG1 strain containing either the plasmid pARA14, or the plasmid pARA15.

5 and 10-ml cultures, in LB broth supplemented with 100 µg of ampicillin per ml, were inoculated with 250 µl of a culture saturated with *E. coli* TG1 containing either pARA 14, or pARA 15. After culturing for one hour, with stirring, at 37° C., the cells were harvested by centrifugation and subjected to an osmotic shock. The osmotic fluid thus obtained, in a volume of 400 µl, contains the entire β-lactamase produced.

On each of the fluids, the total quantity of proteins is measured and the β-lactamase activity is assayed. The latter is performed according to the procedure described by O'CALLAGAN et al. (Antimicrobial Agents and Chemotherapy, 1972, 1, 283–288), using Nitrocefin (Oxoid) as substrate.

The results are represented in Table I below:

TABLE I

| PLASMID | Total volume of culture | $OD_{600}$ at the end of the culture | β-LACTAMASE ACTIVITY | |
|---|---|---|---|---|
| | | | U/ml of osmotic fluid | U/mg of proteins in the osmotic fluid |
| pARA14 | 5 | 0.45 | 0.26 | 5.3 |
| | 10 | 0.25 | 0.3 | 4.1 |
| pARA15 | 5 | 0.44 | 5.39 | 108 |
| | 10 | 0.18 | 3.21 | 60 |

It is known that the expression of the bla gene is constitutive. The production of β-lactamase in the exponential growth phase is therefore directly proportional to the copy number of the gene, and therefore of the plasmid carrying it.

It can be concluded therefrom that the *E. coli* TG1 strain which carries pARA15 harbours 15 to 20 times more copies of plasmid than the *E. coli* TG1 strain which carries pARA14, under identical culture conditions.

b) Expression of the β-galactosidase gene

Two constructions were tested: one with the β-galactosidase gene alone in pLM3, the other with the β-galactosidase gene fused downstream of the protease gene of the HIV 1 virus in the plasmid pARA 15 (pARA15PR107β-gal).

The control plasmids are, on the one hand, pUC 9 and, on the other hand, the plasmid pARA14PR107β-gal which differs from pARA15PR107β-gal only in its replication origin, which is that of the "wild type", of pBR322).

Procedure for the assay of β-galactosidase: 5 ml of LB medium supplemented with 100 µg of ampicillin per ml, were inoculated with 250 µl of a saturated culture and then incubated, with stirring, at 37° C. When the $OD_{600}$ reaches 0.4, the induction is performed with 2 mM of IPTG for the strains harbouring pCU9 or pLM3, or 0.2% arabinose for the strains harbouring pARA14PR107β-gal or pARA15PR107β-gal. The β-galactosidase activity is then assayed in culture samples collected at various incubation times (0 min, 40 min, 120 min.).

Under these conditions, and at the end of 2 hours of incubation, the β-galactosidase level obtained in the cellular pellets is about 16 to 20 times greater with pLM3 than with pUC9, and about 2.5 times higher with pARA 15 than with pARA 14.

For these latter two plasmids, measurement of the expression of the β-galactosidase gene makes it possible to know the level of increase in the production of the HIV-1 protease in the *E. coli* MC1061 strain harbouring these plasmids. This protein is difficult to produce in *E. coli*, being that it is reputed to be toxic for the bacterium. The increase in production by a factor of 2.5 is therefore highly significant.

---

We claim:

1. A DNA sequence derived from a ColE1-type replication origin having the nucleic acid sequence of SEQ ID NO:1 with a guanine to adenine transition at position 2976.

2. A DNA sequence derived from a ColE1-type replication origin having the nucleic acid sequence of SEQ ID NO:1 with a deletion of a guanine at position 3057.

3. The DNA sequence according to claim 2, wherein said DNA sequence further has a guanine to adenine transition at position 2976.

4. A plasmid comprising a DNA sequence derived from a ColE1-type replication origin having the nucleic acid sequence of SEQ ID NO:1 with a guanine to adenine transition at position 2976.

5. A plasmid comprising a DNA sequence derived from a ColE1-type replication origin having the nucleic acid sequence of SEQ ID NO:1 with a deletion of a guanine at position 3057.

6. The plasmid of claim 5, wherein said DNA sequence further has a guanine to adenine transition at position 2976.

7. A process for the multiplying a plasmid comprising a DNA sequence derived from a ColE1-type replication origin having the nucleic acid sequence of SEQ ID NO:1 with a guanine to adenine transition at position 2976, said process comprising the steps of:

transforming a host bacterial strain with said plasmid, and culturing said bacterial strain.

8. A process for multiplying a plasmid comprising a DNA sequence derived from ColE1-type replication origin having the nucleic acid sequence of SEQ ID NO:1 with a deletion of a guanine at position 3057, said process comprising the steps of:

transforming a host bacterial strain with said plasmid, and culturing said bacterial strain.

9. A process of claim 8, wherein said DNA sequence further has a guanine to adenine transition at position 2976.

10. A process for the amplification of a DNA sequence derived from a ColE1-type replication origin having the nucleic acid sequence of SEQ ID NO:1 with a guanine to adenine transition at position 2976, comprising:

inserting said DNA sequence into a plasmid, transforming a host bacterial strain with said plasmid, and culturing said bacterial strain.

11. A process for the amplification of a DNA sequence derived from a ColE1-type replication origin having the nucleic acid sequence of SEQ ID NO:1 with a deletion of a guanine at position 3057 comprising:

inserting said DNA sequence into a plasmid, transforming a host bacterial strain with said plasmid, and culturing said bacterial strain.

12. A process of claim 11, wherein said DNA sequence further has a guanine to adenine transition at 2976.

13. A process for producing a polypeptide, comprising:

preparing a plasmid comprising (1) a DNA sequence derived from a ColE1-type replication origin having the nucleic acid sequence of SEQ ID NO:1 with a guanine to adenine transition at position 2976, and (2) a gene encoding said polypeptide, transforming a host bacterial strain with said plasmid, and culturing said bacterial strain to obtain said polypeptide.

14. A process for producing a polypeptide, comprising:

preparing a plasmid comprising (1) a DNA sequence derived from a ColE1-type replication origin having the nucleic acid sequence of SEQ ID NO:1 with a deletion of a guanine at position 3057, and (2) a gene encoding said polypeptide, transforming a host bacterial strain with said plasmid, and culturing said bacterial strain to obtain said polypeptide.

15. The process of claim 14, wherein said DNA sequence further has a guanine to adenine transition at position 2976.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 120 base pairs
        ( B ) TYPE: nucleic acid
        ( C ) STRANDEDNESS: unknown
        ( D ) TOPOLOGY: unknown     ( i i ) MOLECULE TYPE: DNA (genomic)

( x ) PUBLICATION INFORMATION:
        ( H ) DOCUMENT NUMBER: WO 93/01293 A1
        ( I ) FILING DATE: 10-JUL-1992

( x i ) SEQUENCE DESCRIPTION: SEQ ID NO:1:

```
TAGAAGGACA  GTATTTGGTA  TCTGCGCTCT  GCTGAAGCCA  GTTACCTTCG  GAAAAAGAGT    60

TGGTAGCTCT  TGATCCGGCA  AACAAACCAC  CGCTGGTAGC  GGTGGTTTTT  TTGTTTGCAA   120
```

( 2 ) INFORMATION FOR SEQ ID NO:2:

( i ) SEQUENCE CHARACTERISTICS:

(A) LENGTH: 119 base pairs
(B) TYPE: nucleic acid
(C) STRANDEDNESS: unknown
(D) TOPOLOGY: unknown (ii) MOLECULE TYPE: Other nucleic acid;
(A) DESCRIPTION: mutant DNA (x) PUBLICATION INFORMATION:
(H) DOCUMENT NUMBER: WO 93/01293 A1
(I) FILING DATE: 10-JUL-1992

(xi) SEQUENCE DESCRIPTION: SEQ ID NO:2:

```
TAGAAGAACA  GTATTTGGTA  TCTGCGCTCT  GCTGAAGCCA  GTTACCTTCG  GAAAAGAGT      60
TGGTAGCTCT  TGATCCGGCA  AACAAACACC  GCTGGTAGCG  GTGGTTTTTT  TGTTTGCAA     119
```